United States Patent [19]
Bennett et al.

[11] Patent Number: 5,520,886
[45] Date of Patent: *May 28, 1996

[54] EXPLOSION RESISTANT REINFORCED CONTAINER ASSEMBLIES FOR MATERIALS TO BE MICROWAVE HEATED

[75] Inventors: Jonathan P. Bennett, Charlotte; Wyatt P. Hargett, Matthews, both of N.C.

[73] Assignee: CEM Corporation, Matthews, N.C.

[*] Notice: The term of this patent shall not extend beyond the expiration date of Pat. No. 5,427,741.

[21] Appl. No.: 183,192

[22] Filed: Jan. 14, 1994

Related U.S. Application Data

[63] Continuation-in-part of Ser. No. 64,753, May 19, 1993, Pat. No. 5,427,741.

[51] Int. Cl.$^6$ .................... B01L 3/00; G01N 25/00
[52] U.S. Cl. .................... 422/102; 219/756; 422/78; 428/363
[58] Field of Search .................... 422/78, 99, 102, 422/103, 113, 295, 296, 104; 219/10.55 E, 756; 428/36.3, 36.6

[56] References Cited

U.S. PATENT DOCUMENTS

| | | | |
|---|---|---|---|
| 4,222,494 | 9/1980 | Lee, Jr. et al. | 220/66 |
| 4,282,504 | 8/1981 | Tobin | 337/186 |
| 4,886,699 | 12/1989 | Caroll et al. | 428/228 |
| 4,904,450 | 2/1990 | Floyd | 422/113 |
| 4,933,526 | 6/1990 | Fisher et al. | 219/10.55 M |
| 4,950,532 | 8/1990 | Das et al. | 428/290 |
| 5,190,809 | 3/1993 | Marissen et al. | 428/225 |
| 5,204,065 | 4/1993 | Floyd | 427/113 |
| 5,230,865 | 7/1993 | Hargett et al. | 422/102 |

OTHER PUBLICATIONS

Dupont Kevler Publication, 15 pages.

*Primary Examiner*—James C. Housel
*Assistant Examiner*—Robert Carpenter
*Attorney, Agent, or Firm*—Raymond F. Kramer

[57] ABSTRACT

Sealable container assemblies include containers for materials which are to be microwave heated, such as in digesting or extracting operations, made of thermoplastic material, such as fluoropolymer, that is strengthened by reinforcing means that may be a fiber reinforced thermoplastic of high tensile strength, such as polyetherimide, with reinforcing continuous fibers in a matrix of such thermoplastic, which fibers are very preferably in the shape of a sleeve or sleeves and are of glass or other heat resistant and microwave transmissive material. The containers may be strengthened by incorporating the fiber reinforced thermoplastic in a wall or walls of the container or preferably by inserting the container into a reinforcement, which is a sleeve or collar of the reinforced thermoplastic. In both such constructions the reinforcing means protects the container against radial failure due to pressure that is generated by the microwave heating of the container contents. However, it has been found that in those cases wherein the internal pressure of the container rises even higher than that against which the reinforcement is protective, failure of the side wall and the reinforcement may be explosive, so the containers of this invention are of a structure that causes them to fail at an unreinforced location before the reinforcement, which failure is less explosive and less damaging to equipment employed and to any surroundings. Also described are the container construction, which preferably includes a central bottom depression and a skirt, and procedures for utilizing the containers in heatings of materials.

17 Claims, 4 Drawing Sheets

EXPLOSION RESISTANT REINFORCED CONTAINER ASSEMBLIES FOR MATERIALS TO BE MICROWAVE HEATED

This application is a continuation-in-part of Ser. No. 08/064,753, filed May 19, 1993, now U.S. Pat. No. 5,427, 741.

This invention relates to pressure resistant reinforced containers that may be subjected to high internal pressures during microwave heatings of their contents, which containers include means for mitigating explosions that can result from failures thereof. More particularly, the invention is of containers having reinforcements about them that act as confining means or sleeves, to support the container walls, which are of yieldable thermopolymer, which containers are of a diminished tendency to fail explosively, so damages due to container failures are reduced.

The manufacture of container assemblies that are protected against failure at high pressures and elevated temperatures is described in parent application Ser. No. 08/064, 753, now U.S. Pat. No. 5,427,741 and in its equivalent Canadian and European Patent Organization applications, No's. 2,123,365 and 94303560.0, respectively which are incorporated herein by reference. Also, the assemblies of this invention will be marketed by CEM Corporation, Matthews, North Carolina, under their designation Advanced Composite Vessel (ACV) and will be described in their manufacturer's bulletin entitled ACV Advanced Composite Vessel for Microwave Sample Preparation, to be published in 1994, after the filing of this patent application.

As was mentioned in the parent patent, for cylindrical containers and other tubular containers the forces exerted on the container structure due to internal pressure buildup, such as occurs when contents are heated, are primarily on the containers' side walls and not on the ends of the containers. In the invention of parent patent 5,427,741 the container side wall was strengthened (or supported) to make the container more resistant to failure under higher internal pressures, thereby permitting heatings of contents thereof to higher temperatures. The bottom of such a container was thickened so as to withstand the mentioned pressures. Such thickenings of the container bottoms could be effected more economically than thickenings of the side walls because of the lesser areas and volumes involved. Although the invention of the parent application was successful and enabled one to operate at higher temperatures and pressures than theretofore, unfortunately, in some instances, when due to operator inattention or malfunctioning equipment the temperature was allowed to increase to substantially above design level, failure of the container could occure, caused by the excess pressure. Such failure was radial failure and in some cases was explosive in nature. To prevent such explosive failures, rare as they might be, and to make the use of the present apparatuses and systems virtually foolproof are objects of the present invention. Thus, users of the container assemblies will have this additional line of protection against the hazard of explosion occurring in their laboratories or on their premises.

The solution to the problem of high pressure radial failure of the reinforced container assemblies of the parent application, as described for the present invention, is not further to strengthen container walls (which include the side walls of the cylindrical container and the container bottom and sealing top). Rather, the container, including the bottom thereof, and the side, too, is made of a yieldable thermopolymer, preferably a fluoropolymer in preferred embodiments of the invention, which will be of such thickness(es) so that it will yield and vent more gradually than the reinforced polyetherimide of the reinforcing means for the container side wall. In actual tests of the invented container assemblies, using such a yielding polymer, such distortions of the container wall (inclusive of the bottom) and more gradual escapings of container contents through openings in unreinforced container parts were noted when the contents were heated to excessively high temperatures. The failures of the containers were non-explosive and although digestions and extractions being undertaken were ruined and the equipment had to be cleaned and restored to working order, no permanent damage was done to the apparatus except to the container that was ruptured, so that digestions, extractions and other heating procedures could be resumed shortly thereafter. Best of all, there were no injuries to personnel and no alarming explosions, so normal operations of the laboratory or other facility could be resumed promptly.

In accordance with the present invention a reinforced sealable cylindrically walled container assembly embodiment thereof which is microwave transmissive and is sealable at an openable top of said container by means for closing is provided, which container can comprise an upper shoulder portion, a side wall that is reinforced against rupture failure due to internal pressure in the container at elevated temperature, by a cylindrical reinforcing sleeve around said side wall of the container, and a bottom which is of a strength less than that of the reinforced container side wall, so that any failure of the container will be through said bottom, which sleeve is of a continuous thermoplastic matrix containing continuous fibrous reinforcement, and a top for the container adapted to be held in sealing engagement with the container upper shoulder portion by a means for closing.

In an embodiment of the invention wherein the container side wall is internally reinforced a reinforced container for material that is to be heated by microwave radiation can comprise a cylindrically walled container that comprises a cylindrical container side wall, an integral bottom, a top for sealing the container, reinforcing fibrous material in said container side wall, which cylindrical side wall, bottom and top are of microwave transparent material or of essentially microwave transparent material, and which reinforcing fibrous material reinforces the container side wall so as to prevent rupture thereof at a temperature of 200° C. and an internal container pressure above 200 lbs./sq. in., with the rest of the container being capable of withstanding an internal container pressure of 200 lb./sq. in. except for at least one portion of said rest of the container which fails at an internal container pressure lower than that at which the reinforced container side wall fails.

For best results the container is of a fluoropolymer, such as TEFLO® PFA, and the reinforcement is in the form of a cylindrical tube of polyetherimide (PEI) with continuous sleeves of glass fibers or yarns molded therein, and the container will fail non-explosively at a pressure above 300 lbs./sq. in. at 200° C. and below the pressure at which the reinforcement fails, which pressure is preferably above 1,000 lbs./sq. in. Also within the invention are various processes in which materials are microwave heated in the container assemblies, which processes include digestions, extractions, chemical reactions and other processes involving microwave heating.

BRIEF DESCRIPTION OF THE DRAWINGS

The invention will be readily understood by reference to this specifciation, including the claims, taken in conjunction with the drawing, in which:

Figure 1:
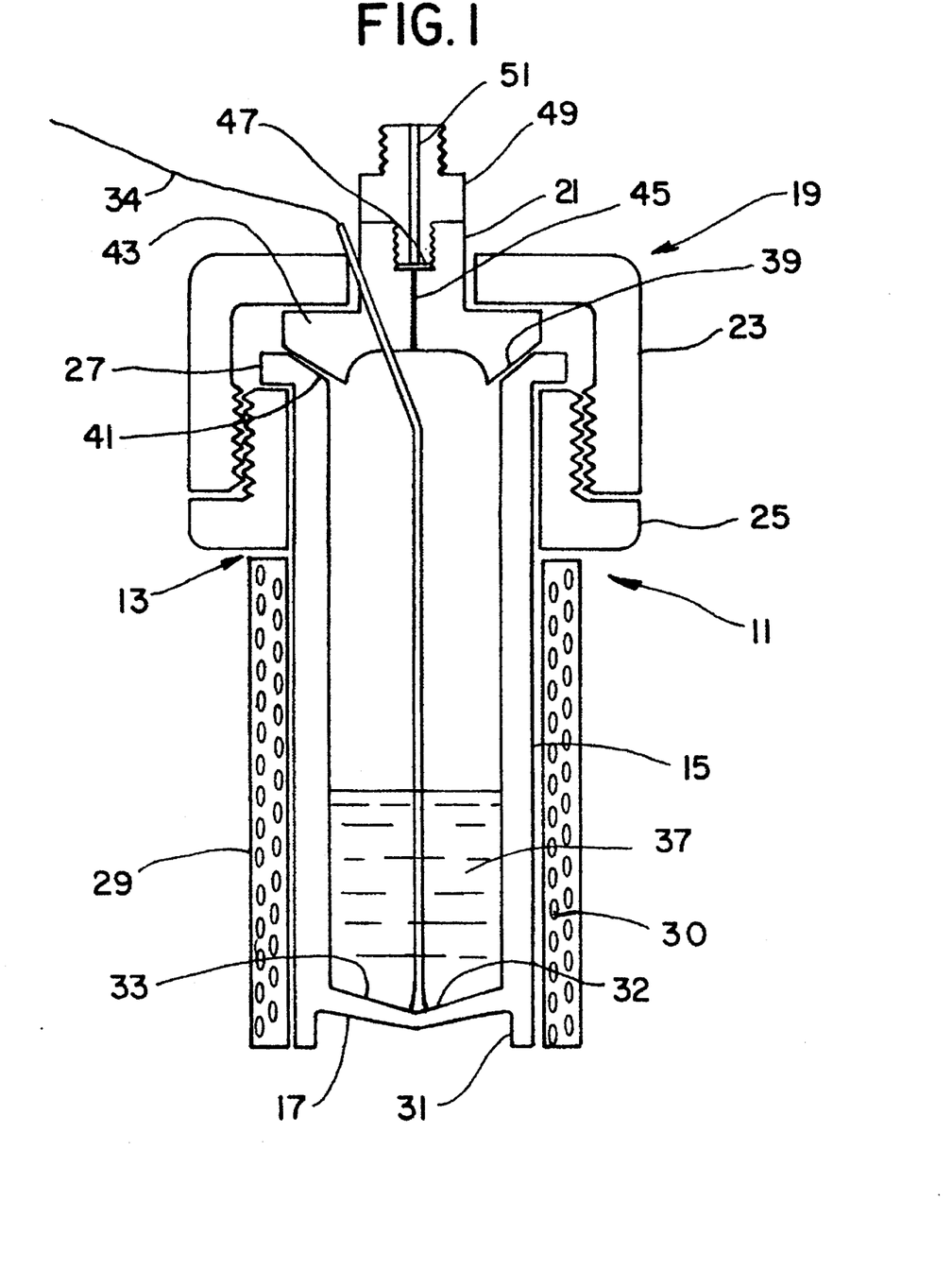
FIG. 1 is a central sectional elevational view of an assembly of this invention (with parts shown slightly separated for clarity of illustration) in which a reinforced sleeve strengthens a container for material to be microwave heated.

In FIG. 1 there is shown a sealable container assembly 11 which includes sealable container 13, which comprises a cylindrical side wall 15 and a bottom 17. The top of the container is open and is sealable by a top 19. The top, for the purposes of this description, includes a seal cover 21, a cap (which may also be referred to as a collar) 23, and a collar 25, which is adapted to bear against flange 27 of container 13. About container 13 is a composite sleeve 29, which is made of suitable high strength thermoplastic, such as polyetherimide, further strengthened by incorporation therein, by molding, of strengthening sleeves 30, preferably of braided or woven yarn of of continuous fibers. Glass fibers or yarns are preferred but quartz and aramide are also useful. The composite sleeve 29 extends from near the bottom of top 19 (the bottom of collar 25) to below the bottom of the container volume and will usually fit about the container in non-binding relationship before heating thereof is commenced. The clearance between the reinforcement 29 and the container 13 is slight, usually being in the range of 0.1 to 2 mm, preferably 0.1 to 0.5 mm, to facilitate sliding of the reinforcement into place. The clearance also allows a slight distortion or expansion of the container under sub-failure pressures, so that it is pressed against the reinforcement, so as to strengthen the container wall. In use the reinforcement 29 will extend to or near to the bottom of skirt 31 of container 13. Container bottom 17 is shaped so as to have a depression 33 in a central portion thereof, which allows improved contact of temperature measuring probe 32 with vessel contents 37 when only a small amount of such a material is being heated. Probe 32 is connected to a monitor or recorder, not illustrated, by wire 34. The presence of skirt 31 facilitates distortion downwardly of the container bottom 17, at depression 33 or at the outer part of bottom 17 and thereby promotes a more gradual failure of the container and slower release of contents from it upon failure.

The seal cover 21, which is adapted to have its contacting surface 39 pressed tightly against a matching surface 41 of container 13 when the assembly is in use, comprises a body portion 43 which includes a venting passageway 45, a rupture disc 47 and holding means 49 for holding the rupture disc in position, which holding means includes a passageway 51 for allowing the escape of gas (and liquid) from the container when the rupture disc fails, due to excessive pressure in the container. The present containers may omit the rupture disc protection in some instances, in which case seal cover 21 may be solid and the holding means may be omitted, too (as when both the container and the seal cover are threaded And screwed together). In such instances the temperature probe is also often omitted. Even when the rupture disc is in place there is still a possibility of explosive failure of the container of the reinforced assembly unless the present invention is utilized, as when the exit passageway 45 is blocked by particulate material being discharged through it or when the rate of discharge through said passageway is too slow to relieve the pressure generated in the container.

Although the containers of the invented assemblies may be of any of various sizes so as to best to fit them for the heating operations being undertaken, usually they will be in the 50 to 200 cu. cm, volume range, preferably about 80 to 140 cu. cm, e.g., 110 cu. cm. The side wall thickness will usually be in the range of 2 to 6 mm and the reinforcement will usually be 1 to 5 mm thick, with the clearance between them usually being in the range of 0.2 to 2 mm. The bottom thickness will often be in the range of 3 mm to 1 cm and the skirt height will usually be in the range of 2 mm to 2 cm.

Figure 2:
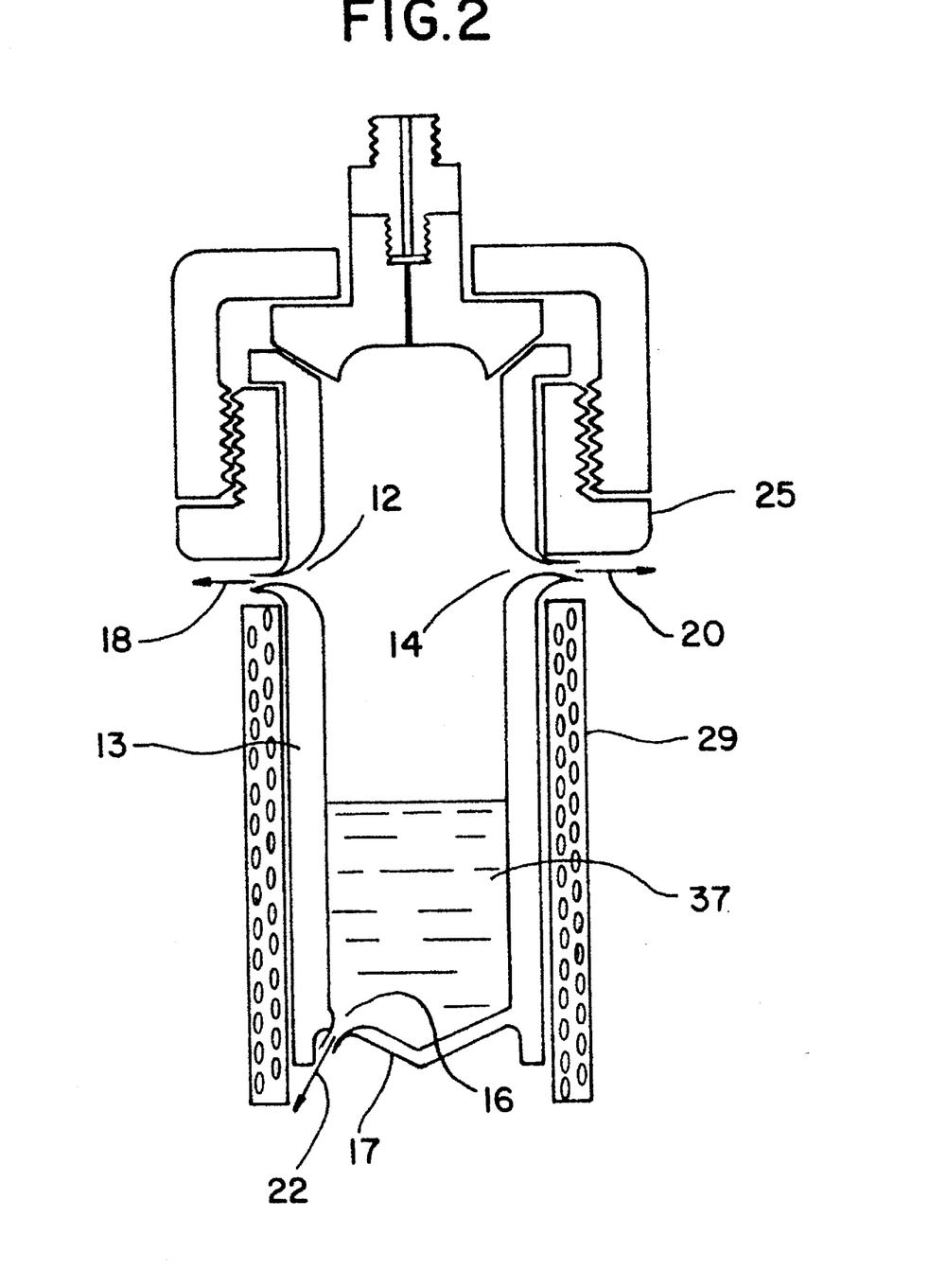
FIG. 2 is a view like that of FIG. 1, illustrating how a container of the assembly may fail under excessive internal pressure.

FIG. 2 illustrates the discharge of vessel contents 37 through openings in container 13 when the pressure in the container 13 is sufficient to cause such failure and is below the failure pressure for the reinforcement 29. The exit paths of container contents are shown by arrows 18, 20 and 22, respectively. Such failure of the container is non-explosive in most cases and even when it might be considered as explosive or near explosive the failure will be less harmful than that which would have occurred had the container been strong enough to remain intact when the pressure in the container was high enough so that the side reinforcement would fail explosively. As is shown, the contents are discharged but the discharge force is somewhat suppressed or mitigated by the release of contents through openings 12, 14 and 16 or any one of them. In part, that is due to the relatively slow enlargement of the opening in the fluoropolymer. The result is a less violent discharge of contents at relatively high container pressures than would have been the case had the container bottom been of a strength greater than, that of the container side, as strengthened by the described reinforcement, or as would have been the situation if the container side had been of a non-yielding material of construction. In FIG. 2 the yielding container locations are at the outer part of the bottom 17 in one case and between reinforcement 29 and collar 25 in the other, at which locations such container ruptures often occur. In both situations the release of contents and the accompanying shocks are diminished further by resistance to moving upwardly in the first case and by the restriction between collar 25 and reinforcement 29 and the resistance of reinforcement 29 to downward movement in the other case.

Figure 3:
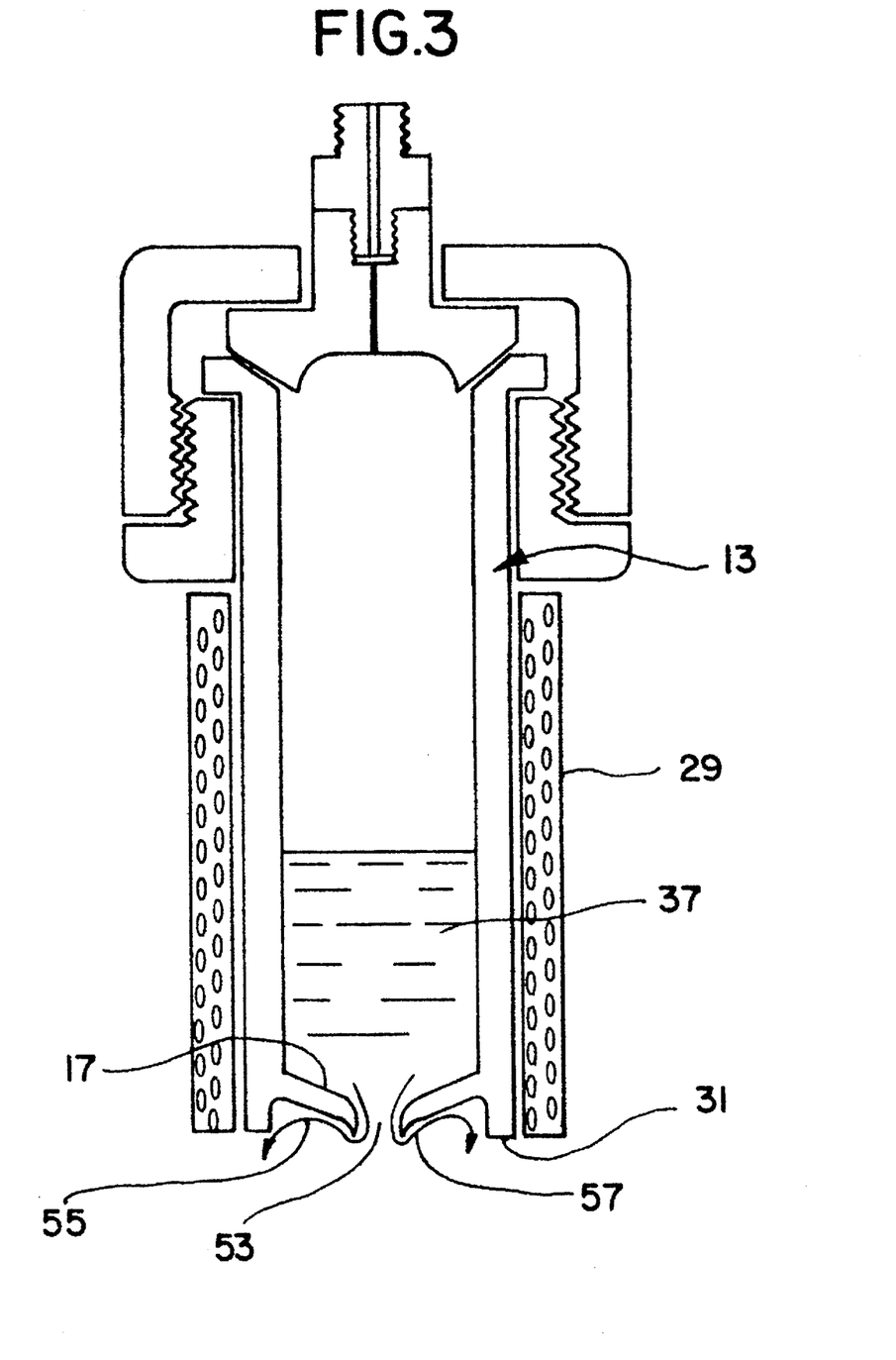
FIG. 3 is a view like that of FIGS. 1 and 2, illustrating a different location on the container of the pressure failure.

In FIG. 3 there is shown an alternative construction of the container assembly, in which the container bottom 17 is made to fail at a weaker (.than the reinforced side) central part thereof. The arrows 55 and 57 show the path of the contents being discharged through opening 53 that is created when the bottom fails due to excessive internal container pressure. The shock of the failure is mitigated by the initial confinement of the discharged contents in the volume under the container, bounded by skirt 31, and by the resistance of the container assembly to upward motion.

Figure 4:
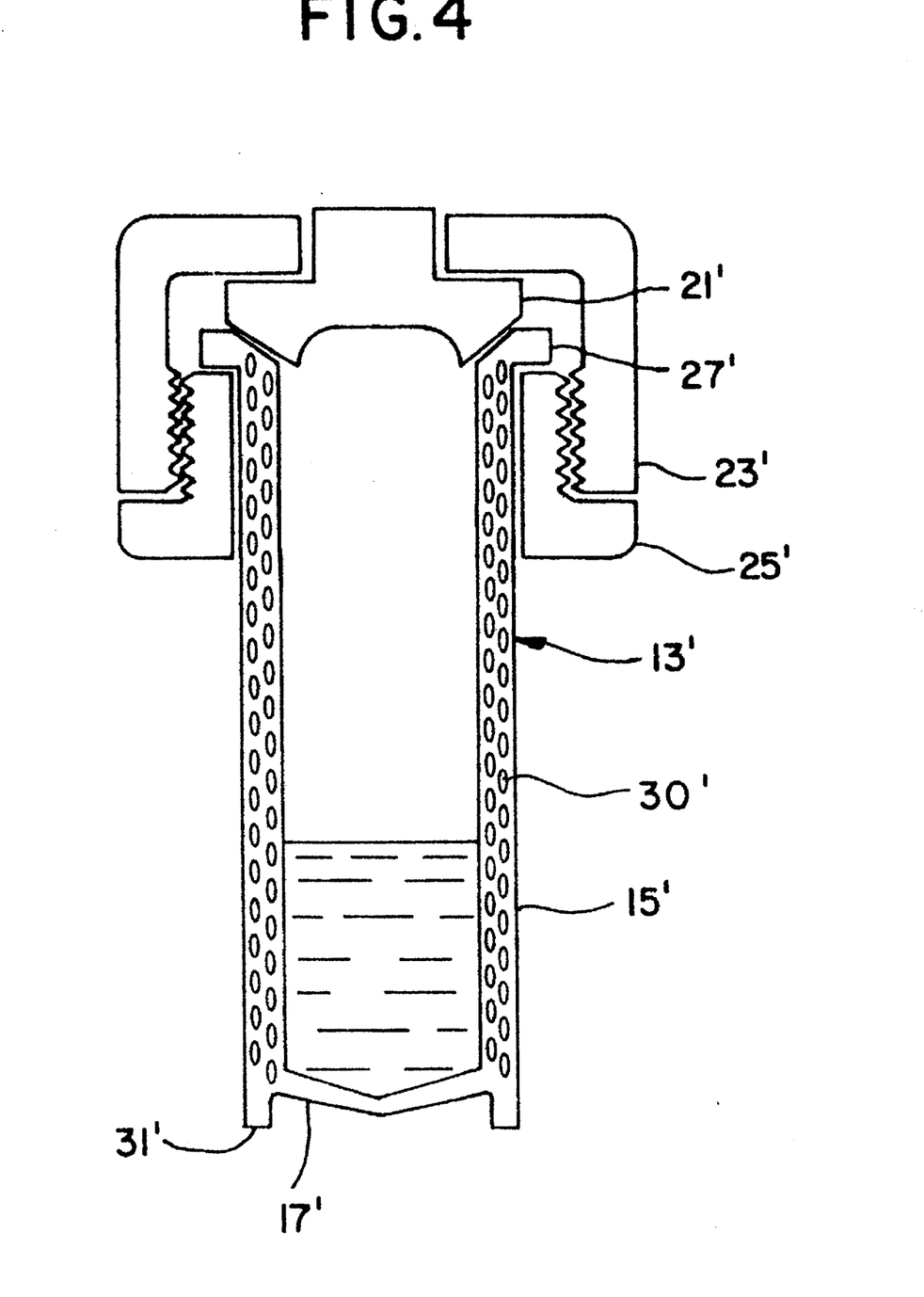
FIG. 4 is a central sectional elevational view of an alternative reinforced container.

In FIG. 4 there is shown a container 13' like that of the assembly of FIG. 1 except for the omission of the reinforcement or strengthening sleeve 29, the presence of a single seal cover 21', which has no rupture disc, passageway or temperature probe in it, and the inclusion of the strengthening sleeve material 30' in the container side wall instead of in a separate reinforcement. Container 13' includes cylindrical side wall 15', flange 27' and skirt 31'. Side wall 15' includes reinforcing sleeves 30' of braided glass yarns in polyetherimide base. In this embodiment of the invention, which is not considered to be as commercially practicable as that of FIG. 1, the reinforced side wall of the container may be produced in the same manner as the reinforcement of FIG. 1, with other operations being utilized to add the flange 27', the bottom 17' and the skirt 31'. The production of reinforced composite Sleeve 29 is described in parent application Ser.

No. 08/064,753, now U.S. Pat. No. 5,427,741, which has been incorporated by reference. Threaded cap 23' and threaded collar 25' seal off container 13' when they are screwed together but alternatively, container 13' and cover 21' may be threaded and screwed together to form a seal.

In a modification of the invention, which is not specifically illustrated in any of FIGS. 1–4, the reinforcement sleeve (the reinforcement) may be coated with fluoropolymer so as to make it more resistant to chemical attack by the material being heated. Also, in another variation, when the container that is reinforced by continuous glass, quartz or aramid fibers therein is made of a polymer that is less resistant to chemical attack than fluoropolymer, such container may be coated internally and/or externally with a fluoropolymer, preferably Teflon PFA, and tube 29 may be of an unreinforced strong polymer.

The materials of construction of the container and the reinforcing means are available commercially and are reasonably priced. The container must be microwave transmissive (transparent or essentially transparent to microwave radiation) and should be resistant to chemical and solvent attacks by materials to be heated therein. Additionally, it should be yieldable, so that it fails gradually when strained, rather than in sudden brittle failure. While various thermopolymers can satisfy such Conditions it has been found that the fluoropolymers, such as sold under the TEFLON trademark, are better than most of the others, and of the various Teflons TEFLON PFA is the best. The Teflons are a group of thermpolymers that are well known in the art. They Are described in an article appearing in *Chemical Engineering* for April, 1993, beginning at page 163, and many of them have been sold under the TEFLON trademark by E. I. dupont de Nemours, Inc., including PTFE (polytetrafluoroethylene), FEP (fluorinated ethylene propylene), PCTFE (polychlorotrifluoroethylene), ETFE (ethylene tetrafluoroethylene), ECTFE (ethylene chlorotrifluoroethylene), PVDF (polyvinylidene fluoride) and PFA (perfluoroalkoxy), of which it is considered that PFA is the best for the purposes of the present invention. Such fluoropolymers have tensile strengths greater than 2,000 lbs./sq. in. at their break points at room temperature and have such tensile strengths greater than 1,000 lbs./sq. in. at 150° C. and 200° C. Additionally, they have melting points and continuous heat resistant temperatures greater than 129° C., with PFA, PTFE, FEP and ETFE having melting points greater than 200° C. and PFA, PTFE and FEP having continuous heat resistant temperatures greater than 200° too. Although the fluoropolymers are highly preferred materials of construction for the containers of this invention when separate reinforcements are employed. and are preferred for reinforcement and reinforced container inner and outer walls too, other thermoplastics, such as ABS, SAN, polyethylene, polypropylene, polycarbonate and injection moldable polyurethane may be employed instead, provided that they are compatible with the processes being practiced.

The polymeric materials that are useful for the matrix for the reinforcing fibers and yarns may be any that are thermoplastic and of sufficient strength and compatibility with the fibers to produce a strengthened composition and assembly under elevated temperature conditions of use. Such use will normally be either digestion or extraction but other operations may also be performed with the reinforced container assemblies of this invention. The thermoplastic will be microwave transmissive, with little or no objectionable absorption (usually less than 5%) of microwave energy from the applied microwave radiation, which will normally be of a frequency in the range of 0.8 to 3 gigahertz. Usually, the tensile strength of such thermoplastic will be at least 1,000 lbs./sq. in. at 150° or 200° C., preferably at least 2,000 lbs./sq. in. at 200° C. and more preferably about 5,000 lbs./sq. in. at such temperature, which temperature is often a maximum temperature or about the highest normal operating temperature for various digestion and extraction processes. Such processes, while capable of being used commercially, are often employed in connection with analytical and laboratory procedures.

Although various other thermoplastics that meet the criteria set forth above, or in some cases less Stringent criteria, may be employed as the matrix for the reinforcing fibers of this invention, including polypropylene, ABS, polystyrene, fluoropolymers and polyacetals, it is highly preferred to employ a polyetherimide (PEI) as such matrix, largely because of its high. tensile strength and its compatibility with reinforcing fibers, such as those of glass, quartz or aramid. Such PEI's are of normal use temperatures for extended periods of employment which are at Least 150° C. and often are at least 200° C., and when they are reinforced by the presence of reinforcing fibers and/or yarns in them (preferably in braid or sleeve form) their strength increases and their maximum continued use temperatures may rise. Various grades of the mentioned thermopolymers can be employed but it will usually be preferable to select the purest of the high quality grades, with the highest tensile strength at elevated temperatures. In most cases that will be a preferred PEI, such as ULTEM® 1000 or ULTEM 1010. The ULTEM's can contain chopped glass fibers (ULTEM's 2100, 2200., 2300 and 2400, for example) but it has been found that such compositions alone do not satisfactorily increase the radial or peripheral tensile strength of a reinforcing means because the short fibers, being discontinuous, do not impart as much strength to the reinforcing means as is wanted. With the continuous yarns, sleeves and braids of the present invention greater strength is obtained and the reinforcing fibers and yarns are oriented to provide the desired reinforcement against peripheral or radial rupture of the reinforced container wall, compared to when unreinforced PEI is utilized in the sleeves.

The reinforcement material for the thermoplastic matrix of the present reinforcing means can be any that is suitable for the present purpose, which sufficiently increases the strength of the matrix material without absorbing objectionable proportions of microwave radiation, so that the protected container for material subjected to pressure during processing operations can withstand the process conditions, which include subjections to elevated temperatures and pressures. Of such materials that are commercially available the best are glass and aramid fibers. Quartz fibers and quartz microfibers are also very good but are expensive and are impractical for many uses because of that fact. The fibers employed are normally of the E Glass or S Glass type, e.g., S-2 Glass, such as are available from Owens-Corning Fiberglas, Inc., but may also be of the aramid type, e.g., K-49 Aramid, available from DuPont. Such glass fibers have tensile strengths at 200° C. of at least 200,000 lbs./sq. in., which is about six times that of steel. The fiber or filament diameter of the glass and aramid will usually be in the range of 0.05 to 1.5 mm, preferably 0.1 to 1 mm, but sometimes, depending on the circumstances, greater and lesser diameters may be utilized. Although individual fibers can be employed as the reinforcing members, provided that they are positioned so as to take the strains to which the devices of the invention are subjected during use, it will usually be preferable for the fibers to be wound in yarns, which in turn, can be formed into sleeves, braids, weaves or nonwoven mats, which are normally the forms that are employed in the composite reinforcing means. The important thing is for a significant proportion of the fiber to be capable of holding a strain in the peripheral direction of the reinforcing means (which is at a right angle to the radii). To accomplish this the fibers or filaments of the braid or weave or other cloth or non-woven pad should desirably have an average component of at least 0.1 in such peripheral direction of strain (as distinguished from an axial component), preferably at least 0.2 (slope) and more preferably, at least 0.4 or 0.5, e.g., 0.7, which is that for a biaxial braid sleeve described in the working examples herein. Of the various types of arrangements of the fibers in the thermoplastic material of the matrix it is preferred to employ biaxial braids for most satisfactory locating of the strengthening fibers with respect to the polymer. The resulting reinforced matrix material will have a tensile strength at 200° C. that will be in excess of 25,000 lbs./sq. in., preferably more than 50,000 lbs./sq. in., and most preferably, more than 75,000 or 100,000 lbs./sq. in. Still, other strengths of the reinforced thermoplastic may be used, depending on the circumstances. The greater the strength of the reinforced polymer the thinner the reinforcing means can be made, while still being capable of withstanding any expected pressure that may be developed in the container during normal use thereof. Thus, for a very strongly reinforced composite a comparatively thin container or reinforcement can be used, with greater ease of handling and operation.

Various relatively minor parts of the invented containers and assemblies may be made from suitable available thermopolymers, of which some that are preferred will now be described. The seal cover of the container, including various parts thereof, will usually be of fluoropolymer. The cap and collar nay be of polypropylene, ABS, polyetherimide (PEI) or other microwave transmissive thermopolymer which maybe reinforced, as by continuous or chopped fibers. Collars 23 and 23' may be extended downwardly to enclose the container or container assembly, if desired, and may include a bottom in some instances. In another embodiment of the invention the extended unfilled collar and bottom or the collar alone may serve as the reinforcing means. In all cases where the part could be in the line of microwave transmission to the container contents the material thereof should not be thermosetting because such plastics are incapable of transmitting such radiation and could interfere with heating of the contents.

In use, the invented assembly of container and reinforcement (or reinforced container alone) is employed for digestions, dissolvings, extractions, reactions and other operations in which the container is under pressure while the contained substance is being heated. Such an apparatus or container and reinforcing meansmay be essentially like those of U.S. Pat. No. 5,230,865 and U.S. Pat. No. 5,427,741, but may be of various other designs and constructions too. The material to be treated and the reagent, digestant or extractant are charged to the PFA container and the container is then connected to any protective apparatus, including a temperature probe, a pressure probe, a rupture disc and other attachments, if appropriate, which connecting is effected by fitting the cover onto the container and tightening the cap onto the collar. Then the microwave radiation of the assembly is begun, preferably onto the container in a microwave system equipped with an oscillating turntable to promote more even heating. The heating is continued long enough to accomplish the assigned task (which time is different for different operations but usually is within a period from 10 minutes to 2 hours). During the heating the pressure in the container may build up to as high as 5,000 lbs./sq. in. but will normally be no higher than 1,000 or 2,000 lbs./sq. in. and preferably is limited to about 500 lbs,/sq. in. and sometimes to about 200 or 300 lbs./sq. in. Because the maximum sustainable strain in use for the glass/PEI composites described is about 75,000 lbs./sq. in., even if a safety factor of 3 was utilized, to sustain an internal pressure in the container of 500 lbs./sq. in. it would take only 1/150 sq. in. of the reinforcement wall cross-section, or only a wall thickness 0.007 in, or 0.2 mm thick. Thus, it is clear that in most instances the reinforcing means should be capable of protecting the protected part of the container against radial failure due to excessive internal pressure. However, although they are very rare, some accidents could occur due to runaway heating and pressure generation in the described containers, such as may be caused by occurrences of chemical reactions, and such can cause explosive radial failures of the reinforcements, which can be extremely harmful to equipment and frightening and dangerous to operating personnel. The designed "softer" or more gentle discharge of container contents by a controlled more gradual failure of the overpressurized container relieves that condition in a more acceptable manner than by radial explosion.

The following examples illustrate preferred embodiments of the invention but do not limit it. Unless otherwise indicated, all parts are by weight and all temperatures are in °C.

EXAMPLE 1

A digestion apparatus of the type illustrated in FIG. 1 is employed to digest corn oil in nitric acid. The digestion container is of PFA (Teflon PFA 340), is 13.2 cm tall and 4.2 cm outside diameter, with a shoulder that is 5 cm across and 7 mm high. The skirt of the container is 1 mm thick and extends downwardly for mm. The container bottom extends downwardly 3 mm to an axial low point, as does the container interior at the bottom. The bottom is 8 mm thick at the container wall and 5 mm thick at the center. The container wall is 4 mm thick so the container volume is about 107 cu. cm. The reinforcement is 4.8 cm o.d. And 4.3 cm i.d. and clears the container by 0.5 mm. It is made by molding a sleeve of fiberglass yarns into a PEI (ULTEM 1000) matrix, as described in U.S. Pat. No. 5,427,741.

The digestion of corn oil described involves treating 0.5 g of corn oil with 10 ml of 10% nitric acid at a temperature of 200° C. for ½ hour, employing a turntable and a microwave apparatus operating at about half power (about 600 watts). The operation is run with 12 such samples and assemblies being employed at a time. The pressures developed average about 200 lbs./sq. in. but in none of the cases mentioned does the rupture disc fail (it is set at 400 lbs./sq. in.) and innone of the cases does the container fail, either at the side or the bottom. However, in some instances, when it is intended to make the container (and reinforcement) "explode" by heating to excessive internal pressures, such failure will occur, through the container, at a location, like one of those shown in FIGS. 2 and 3, but it is not as severe as when the failure is radial and the container is not constructed so as to fail before the reinforcement. Such test results are obtainable by hydrostatic testing techniques and are verifiable by actual use tests. Similar results are obtainable when the invented assemblies are utilized in various extraction operations wherein the mentioned high pressures are developed.

EXAMPLE 2

The tests of Example 1 are repeated, utilizing the strengthened containers of FIG. 4. Essentially the same kinds of results are obtained, with the relatively rare failure of a container being at the unreinforced bottom and being of a less serious nature than it would have been had the failure been radial. The container of this example (and that of Example 1, with the reinforcement about it) withstands radial rupture at internal pressures up to 300 lbs./sq. in. and often up to 1,000 lbs./sq. in. and fails at its bottom at a pressure below that at which the reinforcement fails.

The invention has been described with respect to various illustrations and examples but it is not to be considered as limited to them because one of skill in the art, with the present specification before him or her will be able to utilize substitutes and equivalents without departing from the invention.

What is claimed is:

1. A reinforced sealable cylindrically walled container assembly which is microwave transmissive and is sealable at an operable top of said container by means for sealing which are held tightly to said container by means for closing, which container comprises an upper shoulder portion, a side wall that is reinforced against rupture failure due to internal pressure in the container at elevated temperature, by a cylindrical reinforcing sleeve around said side wall of the container, and a bottom which is of a strength less than that of the reinforced container side wall, so that any failure of the container will be through said bottom, said sleeve is of a continuous thermoplastic matrix containing continuous fibrous reinforcement, and a top for the container adapted to be held in sealing engagement with the container upper shoulder portion by a means for closing.

2. A reinforced sealable cylindrically walled container assembly according to claim 1 wherein the container side wall and bottom are of a fluoropolymer.

3. A reinforced sealable cylindrically walled container assembly according to claim 2 wherein the container side wall and bottom are of a perfluoroalkoxy polymer, the cylindrical reinforcing sleeve is of a polyetherimide matrix reinforced with a glass braid in a form of a sleeve that extends longitudinally within the matrix, the side wall of the container is of a thickness in the range of 2 to 6 mm and the bottom of the container is of a thickness in the range of 3 to 10 mm and greater than the thickness of the side wall of the container the bottom has a depression in a middle portion thereof, and the container side wall terminates at the bottom thereof in a skirt portion which extends 1 to 10 mm below the depressed middle portion of the container bottom.

4. A reinforced container for material that is to be heated by microwave radiation which comprises a cylindrically walled container that comprises a cylindrical container side wall, an integral bottom, a top for sealing the container, reinforcing fibrous material in said container side wall, which cylindrical side wall, bottom and top are of microwave transparent material or essentially microwave transparent material, and which reinforcing fibrous material reinforces the container side wall so as to prevent rupture thereof at a temperature of 200° C. and an internal container pressure above 200 lbs./sq. in., with the rest of the container being capable of withstanding an internal container pressure of 200 lbs./sq. in. except for at least one portion of said rest of the container which fails at an internal container pressure lower that that at which the reinforced container side wall fails.

5. A procedure for heating a liquid state microwave absorptive material which comprises providing the reinforced container of claim 4 and heating said material in said container so that a pressure greater than 200 lbs./sq. in is produced in said container.

6. A reinforced container assembly for containing material that is to be heated by microwave radiation which comprises a cylindrical container having a side wall, an integral bottom and a top for sealing the container, and a reinforced cylindrical sleeve around said container side wall, which sleeve contains reinforcing fibrous material therein, which side wall, bottom and top of the container and which sleeve and fibrous material therein are of microwave transparent or essentially microwave transparent material and which reinforcing fibrous material reinforces the sleeve so as to prevent rupture of the container side wall at a temperature of 200° C. and an internal container pressure above 200 lbs./sq. in., with the rest of the container being capable of withstanding an internal container pressure of 200 lbs./sq. in. except for at least one portion of said rest of the container which fails at an internal container pressure lower than that at which the reinforced container side wall fails.

7. A procedure for heating a liquid state microwave absorptive material which comprises providing the reinforced container assembly of claim 6 and heating said material in said container of said assembly by means of microwave radiation, to a temperature at which a pressure is developed that causes failure of said bottom of said container without failure of said container side wall.

8. A reinforced sealable cylindrically walled container assembly according to claim 6 wherein the fibrous material is selected from the group consisting of glass, aramid and quartz, and mixtures of two or more thereof, the reinforced container side wall is protected by said sleeve against radial rupture at internal container pressures above 300 lbs./sq. in. and the bottom of the container fails at a container internal pressure above 300 lbs./sq. in. and below that pressure at which the container side wall fails.

9. A reinforced sealable cylindrically walled container assembly according to claim 8 wherein the cylindrical sleeve is in contact with the cylindrical container and is reinforced with fibers or yarns of fibrous material in continuous weaves or braids, which extend substantially longitudinally within the cylindrical side wall of the sleeve so that the sleeve withstands an internal pressure in the container, which pressure is transmitted to the sleeve by said contact, of at least 500 lbs./sq. in., thereby protecting said container against rupture of the side wall thereof, and the bottom of the container is of such a construction as to fail at a pressure in the container above 300 lbs./sq. in. and below the pressure at which the reinforced sleeve fails.

10. A reinforced sealable cylindrically walled container assembly according to claim 9 wherein the cylindrical sleeve which reinforces the container side wall is of a thermopolymer matrix that is reinforced with braided yarns in the form of a sleeve or of a plurality of sleeves within the matrix, which braided sleeve or sleeves in the matrix extend longitudinally with respect to the cylindrical sleeve and are substantially coaxial with said cylindrical sleeve.

11. A reinforced container assembly according to claim 9 wherein the reinforcing continuous fibrous material is in the form of a continuous biaxially braided glass sleeve in which braid the slope is at least 0.4, and the matrix of the cylindrical sleeve is of polyetherimide.

12. A reinforced sealable cylindrically walled container assembly according to claim 10 wherein the thermopolymer of the thermopolymer matrix of the cylindrical sleeve is a polyetherimide which is of a tensile strength of at least 5,000 lbs./sq. in. at 200° C., the reinforcing cylindrical sleeve is of a tensile strength of at least 50,000 lbs./sq. in. at 200° C. and the container bottom and side wall are of a fluoropolymer.

13. A reinforced sealable cylindrically walled container assembly according to claim 12 wherein the container bottom has a depression in a middle portion thereof.

14. A reinforced sealable cylindrically walled container assembly according to claim 13 wherein the container bottom and side wall are of perfluoroalkoxy polymer, the side wall of the container is of a thickness in the range of 2 to 6 mm, the bottom of the container is of a thickness in the range of 3 to 10 mm, which is greater than the side wall thickness of the container, the reinforcing cylindrical sleeve is bottomless and is of a thickness in the range of 1 to 5 mm, and an initial clearance between the container and the reinforcing cylindrical sleeve is in the range of 0.2 to 2 mm.

15. A reinforced sealable cylindrically walled container assembly according to claim 14 wherein the container has a shoulder at the top thereof and means for sealing, adapted to seal off said container at the top thereof, which means for sealing are held to the container in sealing engagement by means for closing, which means for closing comprise threaded upper and lower collars adapted to press said means for sealing and the container side together, with said lower collar contacting said shoulder when said collars are screwed together.

16. A reinforced sealable cylindrically walled container assembly according to claim 15 wherein the container side wall further comprises a depending skirt portion at the bottom thereof, on which skirt portion the container is supported during use.

17. A reinforced sealable cylindrically walled container assembly according to claim 16 wherein the depending skirt portion of the container side wall depends in the range of 1 to 10 mm below the depression in the middle portion of the container bottom.

* * * * *